(12) United States Patent
Thompson et al.

(10) Patent No.: US 9,880,112 B2
(45) Date of Patent: Jan. 30, 2018

(54) METHODS AND SYSTEM FOR DETERMINING SHEAR ANGLE

(71) Applicant: The Boeing Company, Chicago, IL (US)

(72) Inventors: Jeffrey G. Thompson, Auburn, WA (US); David S. Nansen, Renton, WA (US); Ronald V. Bulthuis, Des Moines, WA (US); Thomas E. Riechers, Bonney Lake, WA (US)

(73) Assignee: The Boeing Company, Chicago, IL (US)

( * ) Notice: Subject to any disclaimer, the term of this patent is extended or adjusted under 35 U.S.C. 154(b) by 252 days.

(21) Appl. No.: 14/821,267

(22) Filed: Aug. 7, 2015

(65) Prior Publication Data
US 2017/0038313 A1 Feb. 9, 2017

(51) Int. Cl.
*G01N 23/04* (2006.01)
*B32B 3/00* (2006.01)
*G01B 15/00* (2006.01)
*G01N 1/00* (2006.01)

(52) U.S. Cl.
CPC ............ *G01N 23/04* (2013.01); *B32B 3/00* (2013.01); *G01B 15/00* (2013.01); *G01N 1/00* (2013.01); *G01N 2223/33* (2013.01); *G01N 2223/615* (2013.01)

(58) Field of Classification Search
CPC ...... G01N 23/04; G01N 1/00; G01N 2223/33; G01N 2223/615
See application file for complete search history.

(56) References Cited

U.S. PATENT DOCUMENTS

| | | | | |
|---|---|---|---|---|
| 3,090,865 A | * | 5/1963 | Schneeman | G01N 23/043 378/190 |
| 3,351,760 A | | 11/1967 | Brown | |
| 4,969,110 A | * | 11/1990 | Little | G01N 23/046 348/26 |
| 6,047,041 A | * | 4/2000 | Ellinger | G01N 23/02 378/57 |

OTHER PUBLICATIONS

AFRL-ML-WP-TP-2006-477; Comparison of X-Ray, Millimeter Wave, Shearography and Throughtransmission Ultrasonic Methods for Inspection of Honeycomb Composites (Preprint); M.A. Abou-Khousa, A. Ryley, S. Kharkovsky, R. Zoughi, D. Daniels, N. Kreitinger, and G. Steffes Aug. 2006.
Search Report for related European Application No. EP16172864.7; dated Dec. 13, 2016.

* cited by examiner

*Primary Examiner* — Courtney Thomas
(74) *Attorney, Agent, or Firm* — Miller, Matthias & Hull LLP

(57) ABSTRACT

A method for determining an actual shear angle between an interior wall and a facesheet of a cellular panel using an imaging system is disclosed. The imaging system may include a radiation source and a detector diametrically opposed to the radiation source. The method may include positioning the cellular panel at a tilt angle relative to a line extending between the radiation source and the detector, transmitting radiation from the radiation source to the detector through the cellular panel at the tilt angle to obtain an image, measuring a projected shear angle in the obtained image, and determining the actual shear angle between the interior wall and the facesheet using the tilt angle and the projected shear angle.

19 Claims, 14 Drawing Sheets

METHODS AND SYSTEM FOR DETERMINING SHEAR ANGLE

FIELD OF THE DISCLOSURE

The present disclosure relates generally to cellular panels and, more particularly, to shear angle quantification of panels having cells.

BACKGROUND OF THE DISCLOSURE

Some vehicles, such as aircraft, include panels having cells. For example, a panel may be composed of a honeycomb core sandwiched between two facesheets. More specifically, interior cell walls of the honeycomb core are perpendicular to the facesheets. In some situations, the cell walls of the core may move out of perpendicular orientation with the facesheets. The angle between a cell wall and one of the facesheets is referred to as the shear angle. If the shear angle is zero, the cell wall is perpendicular to the facesheet.

Currently, in order to measure the shear angle, the panel is sliced into pieces. Each piece is then examined to determine if the shear angle is greater than zero. Typically, the shear angle is measured by hand. If the shear angle is greater than zero, the forming process for the panels can be adjusted to produce a zero shear angle. Measurements of subsequent panels and further adjustments to the forming process may be made in order to eventually achieve a zero shear angle between the cell walls of the core and the facesheets.

In addition, non-destructive inspection of the panel may be performed using an X-ray system. However, current X-ray inspection techniques are unable to measure the shear angle between the cell walls and the facesheets. Particularly, if the X-ray system collects image data of the core from a view normal to the facesheet, a nonzero shear angle appears the same as a zero shear angle in an image generated from the collected data. Moreover, if the X-ray system collects image data of the core from a view parallel to the facesheet, the X-rays cannot transmit through the entire length of the panel, and thereby cannot produce an X-ray image.

Accordingly, there exists a need for a non-destructive inspection technique that determines the shear angle in the interior of the panels having cells.

SUMMARY OF THE DISCLOSURE

In accordance with one embodiment, a method for determining an actual shear angle between an interior wall and a facesheet of a cellular panel using an imaging system is disclosed. The imaging system may include a radiation source and a detector diametrically opposed to the radiation source. The method may include positioning the cellular panel at a tilt angle relative to a line extending between the radiation source and the detector, transmitting radiation from the radiation source to the detector through the cellular panel at the tilt angle to obtain an image, measuring a projected shear angle in the obtained image, and determining the actual shear angle between the interior wall and the facesheet using the tilt angle and the projected shear angle.

In a refinement, the method may further comprise rotating the radiation source and the detector while the cellular panel is stationary to achieve the tilt angle.

In another refinement, the method may further comprise rotating the cellular panel while the radiation source and the detector are stationary to achieve the tilt angle.

In another refinement, the tilt angle may be between an inclusive range of twenty degrees to fifty degrees (20°-50°).

In another refinement, the method may further comprise using X-ray radiation as the radiation.

In another refinement, the method may further comprise determining if the cellular panel is within predetermined specifications based on the determined actual shear angle.

In another refinement, the method may further comprise calculating the actual shear angle using the tilt angle and the projected shear angle.

In another refinement, the method may further comprise obtaining a first image of a first interior wall at a first location to determine a first actual shear angle, and obtaining a second image of a second interior wall at a second location to determine a second actual shear angle.

In another refinement, the method may further comprise averaging the first actual shear angle and the second actual shear angle to obtain an average shear angle for the cellular panel.

In another refinement, the method may further comprise identifying the projected shear angle between a line perpendicular to the facesheet and a line extending through node welds of the interior wall.

In another refinement, the method may further comprise a user of the imaging system determining the projected shear angle.

In another refinement, the method may further comprise the imaging system automatically determining the projected shear angle using boundary detection.

In another refinement, the method may further comprise placing a reference element on a surface of the facesheet to assist in identification of the line perpendicular to the facesheet.

In accordance with another embodiment, an imaging system for determining an actual shear angle between an interior wall and a facesheet of a cellular panel is disclosed. The imaging system may comprise a radiation source, a detector, and at least one computer processor in operative communication with the radiation source and the detector. The detector may be diametrically opposed to the radiation source and configured to detect radiation transmitted through the cellular panel from the radiation source. The at least one computer processor may be configured to position the radiation source and the detector at a tilt angle relative to a line perpendicular to the facesheet of the cellular panel, transmit radiation from the radiation source through the cellular panel to the detector to obtain an image of the interior wall of the cellular panel, identify in the obtained image the line perpendicular to the facesheet, identify in the obtained image a line parallel to the interior wall, measure in the obtained image a projected shear angle between the line perpendicular to the facesheet and the line parallel to the interior wall, and determine an actual shear angle between the facesheet and the interior wall using the tilt angle and the projected shear angle.

In a refinement, the cellular panel may be positioned closer to the detector than the radiation source.

In another refinement, the at least one computer processor may be configured to use node welds of the interior wall in the obtained image to identify the line parallel to the interior wall.

In another refinement, the at least one computer processor may be configured to use a reference element attached to a surface of the facesheet in the obtained image to identify the line perpendicular to the facesheet.

In accordance with another embodiment, an automated method for determining an actual shear angle between an interior wall and a facesheet of a cellular panel using an imaging system is disclosed. The imaging system may include a radiation source, a detector diametrically opposed to the radiation source, and at least one computer processor in operative communication with the radiation source and the detector. The automated method may comprise moving the radiation source and the detector such that a line extending between the radiation source and the detector is at a tilt angle relative to a line perpendicular to the facesheet, acquiring an image of the interior wall by transmitting radiation from the radiation source through the cellular panel to the detector, identifying in the acquired image a projected shear angle between the line perpendicular to the facesheet and a line extending through node welds of the interior wall, measuring the projected shear angle, and determining an actual shear angle between the facesheet and the interior wall based on the tilt angle and the measured projected shear angle.

In a refinement, the automated method may further comprise using the following equation to determine the actual shear angle:

$$\tan \theta = \tan \alpha * \sin \varphi$$

where θ is the actual shear angle, α is the measured projected shear angle, and φ is the tilt angle.

In another refinement, the automated method may further comprise storing a value for the tilt angle between an inclusive range of twenty degrees to fifty degrees (20°-50°) in a memory associated with the at least one computer processor.

These and other aspects and features will become more readily apparent upon reading the following detailed description when taken in conjunction with the accompanying drawings. In addition, although various features are disclosed in relation to specific exemplary embodiments, it is understood that the various features may be combined with each other, or used alone, with any of the various exemplary embodiments without departing from the scope of the disclosure.

While the present disclosure is susceptible to various modifications and alternative constructions, certain illustrative embodiments thereof will be shown and described below in detail. The disclosure is not limited to the specific embodiments disclosed, but instead includes all modifications, alternative constructions, and equivalents thereof.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. It should be understood that the system described herein can be used with any suitable panel having cells.

Figure 1:
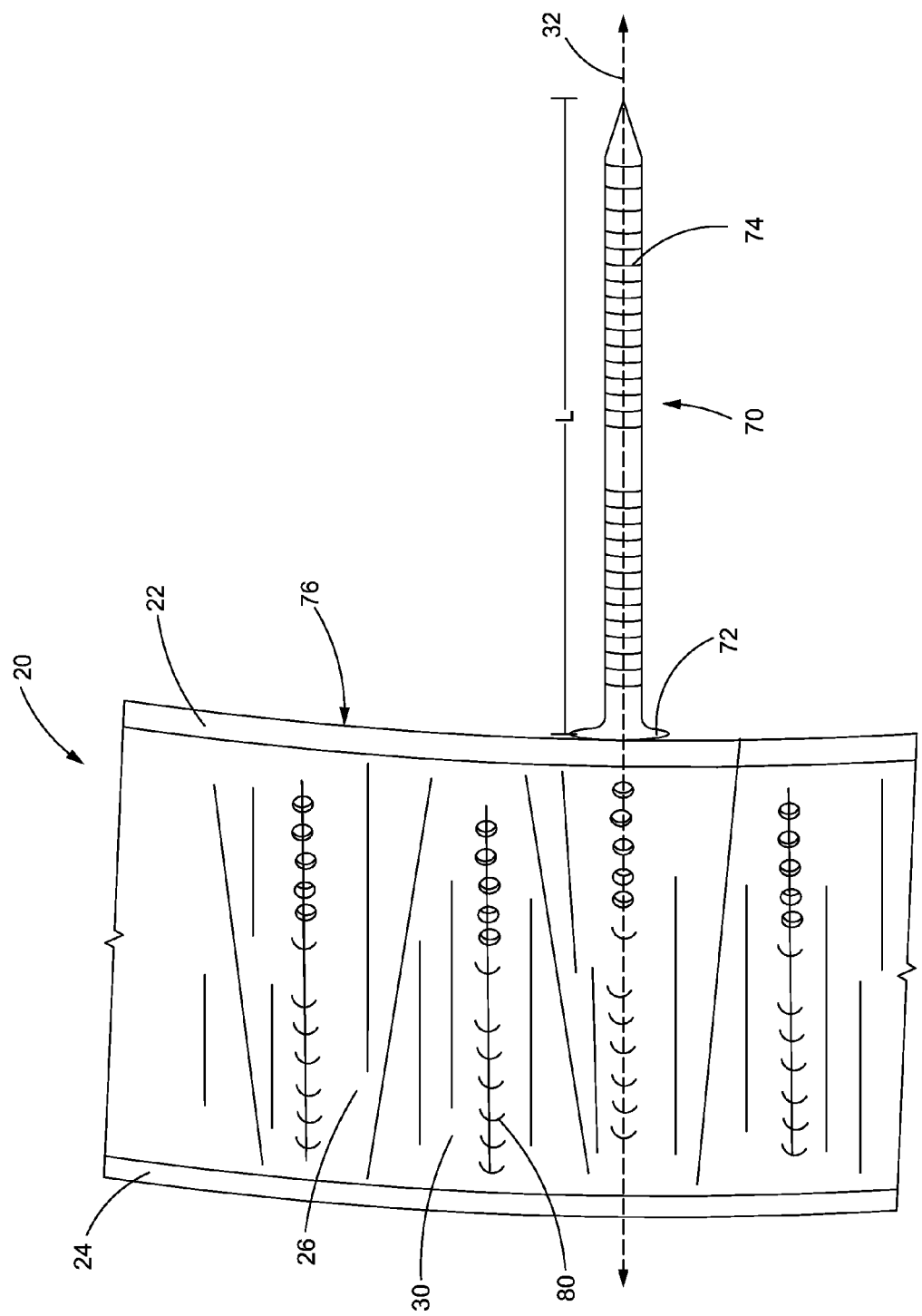
FIG. 1 is a cross-sectional view of part of a cellular panel, in accordance with one embodiment of the present disclosure.
Figure 2:
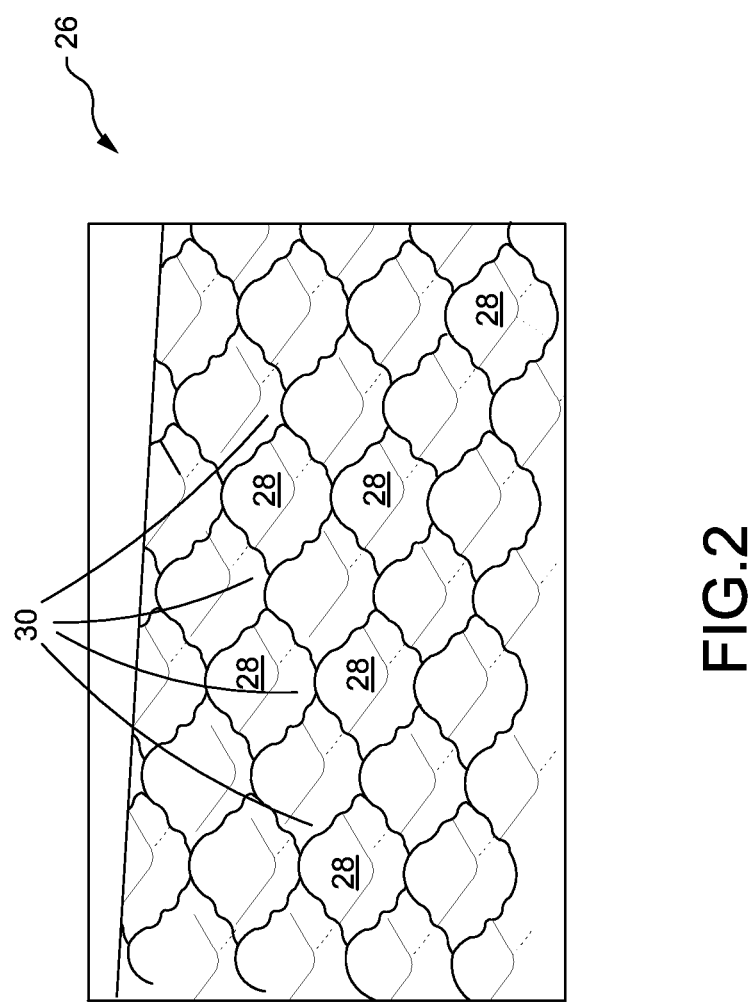
FIG. 2 is a plan view of a core of the cellular panel of FIG. 1.

FIG. 1 illustrates a cross-sectional view of part of a panel having cells, or a cellular panel 20, consistent with certain embodiments of the present disclosure. For example, the cellular panel 20 may be made of composite material, titanium, aluminum, and the like. The cellular panel 20 may include a first facesheet 22 and a second facesheet 24. The second facesheet 24 may be spaced apart from and concentric to the first facesheet 22. A core 26 may be disposed between the first facesheet 22 and the second facesheet 24. As shown in FIG. 2, the core 26 includes a plurality of cells 28, such as cells in a honeycomb configuration, although other configurations may be used for the core 26. Each of the cells 28 are defined by interior walls 30 of the core 26.

Figure 3:
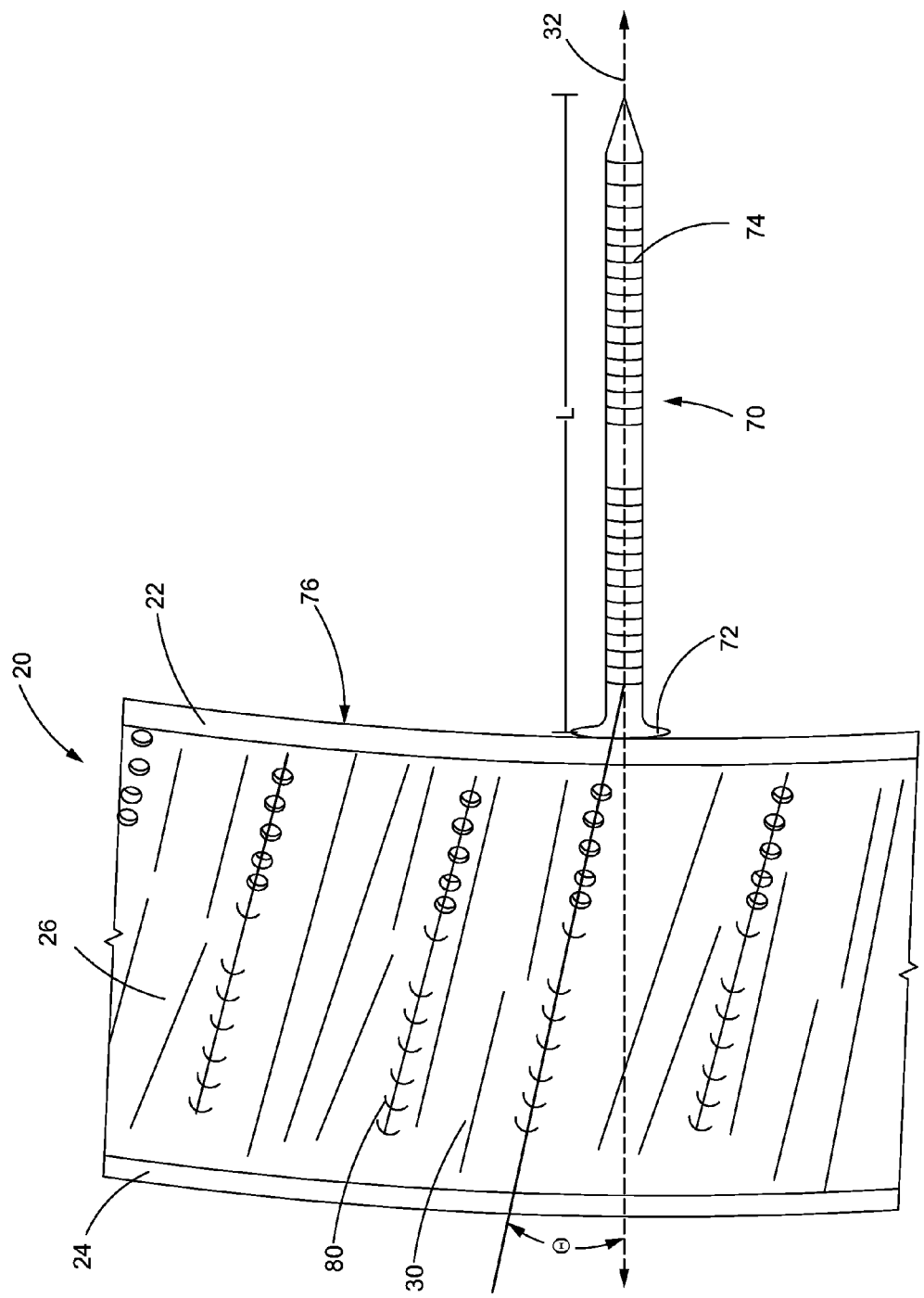
FIG. 3 is a cross-sectional view of part of another cellular panel.
Figure 4:
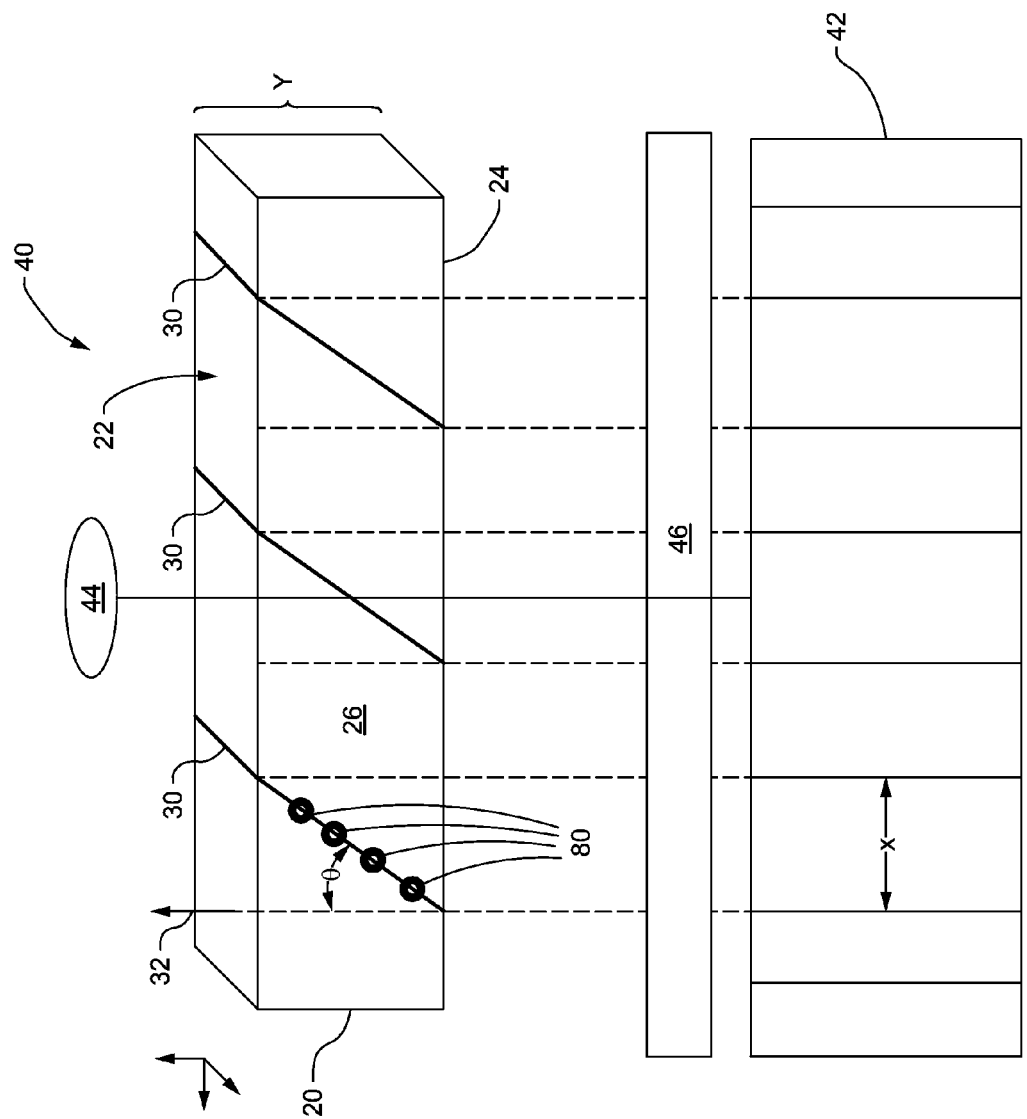
FIG. 4 is a side view of an imaging system, in accordance with another embodiment.

Furthermore, the cellular panel 20 may initially be manufactured such that the interior walls 30 of the core 26 are perpendicular to each of the first facesheet 22 and the second facesheet 24. In some cases, one or more of the interior walls 30 may be disposed at a shear angle θ relative to a line 32 perpendicular to the first facesheet 22 and the second facesheet 24, as shown in FIGS. 3 and 4. As used herein, the shear angle θ refers to an angle between the line 32 perpendicular to the facesheets 22, 24 and an interior wall 30 of the core 26. When the shear angle θ is zero degrees (0°), as shown in FIG. 1, the interior wall 30 is parallel to, coincident, or aligned with the line 32 and perpendicular to the facesheets 22, 24.

As shown in FIG. 4, an imaging system 40 may be used to inspect the cellular panel 20, in accordance with an embodiment of the present disclosure. More specifically, the imaging system 40 can be used to measure or quantify the actual shear angle θ between the interior walls 30 of the core 26 and one of the facesheets 22, 24 by producing an image 42. For example, the imaging system 40 may be configured for radiography, such as, digital or film radiography. However, other types of imaging systems may be used as well.

The imaging system 40 includes a radiation source 44 and a detector 46 diametrically opposed to the radiation source 44. The radiation source 44 is configured to emit X-ray radiation, or other types of radiation, through the cellular panel 20. The detector 46 is configured to detect the radiation transmitted through the cellular panel 20 from the radiation source 44 and to produce an image from the detected radiation. For example, the detector 46 may comprise a digital detector. However, other types of detectors 46, such as film detectors, may be used as well.

From the diagram in FIG. 4, the following equation for the actual shear angle θ is derived:

$$\tan \theta = x/y \quad [1]$$

where θ is the actual shear angle; x is a projected width of the interior wall 30 onto one of the facesheets 22, 24 when a line 50 extending between the radiation source 44 and the detector 46 is parallel to, coincident, or aligned with the line 32 perpendicular to the facesheets 22, 24; and y is a thickness of the cellular panel 20.

Figure 5:
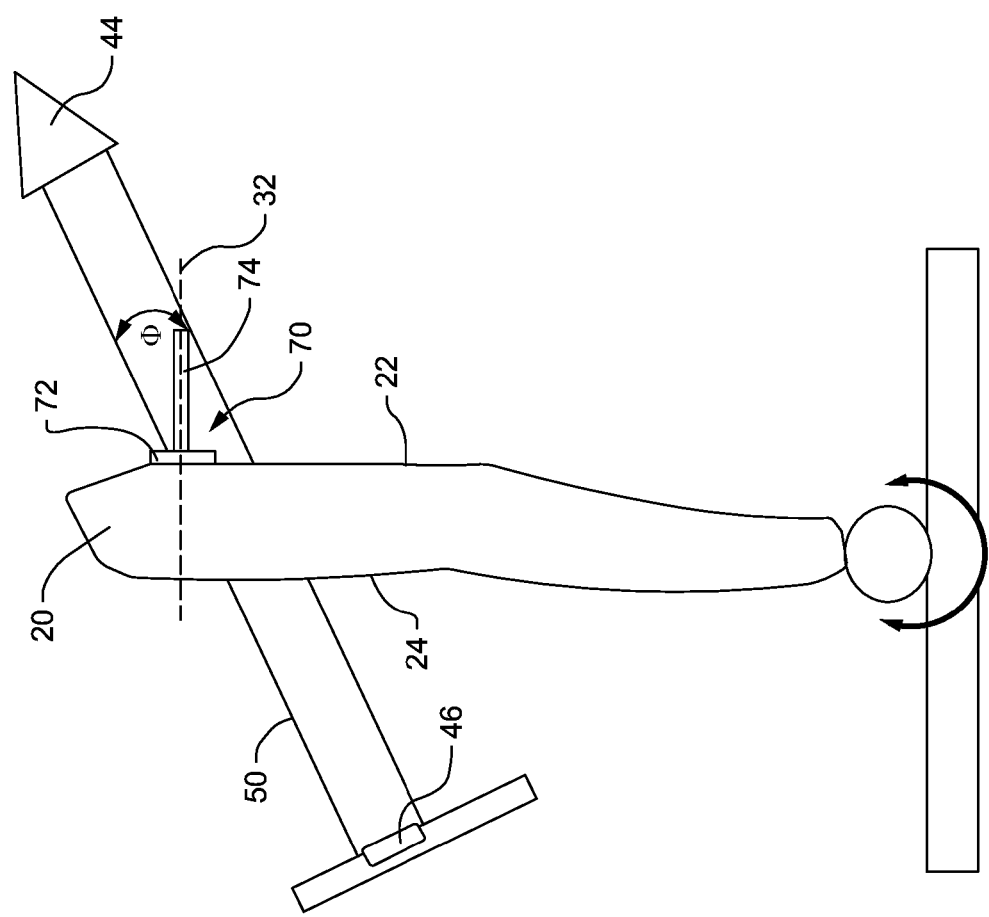
FIG. 5 is a side view of a cellular panel with a radiation source and a detector of the imaging system of FIG. 4 positioned at a tilt angle relative to the cellular panel.

In order to determine the shear angle θ, the cellular panel 20 is positioned at a tilt angle φ relative to the line 50 extending between the radiation source 44 and the detector 46, as shown in FIG. 5. For example, the line 50 may be a straight line transmission path from the radiation source 44 through the cellular panel 20 to the detector 46. As used herein, the tilt angle φ refers to an angle between the line 32 perpendicular to the facesheets 22, 24 and the line 50 extending between the radiation source 44 and the detector 46. When the tilt angle φ is zero degrees (0°), the line 50 is parallel to, coincident, and/or aligned with the line 32 and perpendicular to the facesheets 22, 24.

Figure 6:
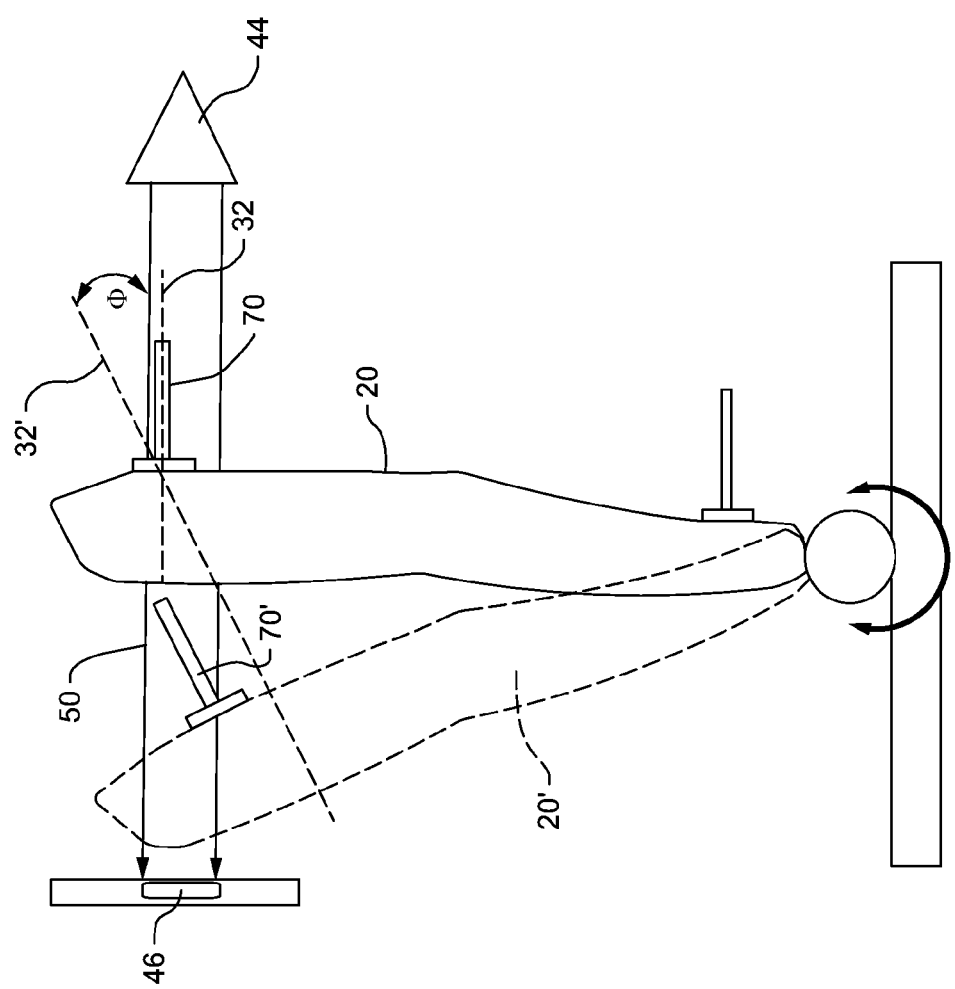
FIG. 6 is a side view of a cellular panel positioned at a tilt angle relative to a radiation source and a detector, in accordance with another embodiment.

For instance, the tilt angle φ may be between an inclusive range of twenty degrees to fifty degrees (20°-50°). However, other values for the tilt angle φ may be used. To achieve the tilt angle φ, the radiation source 44 and the detector 46 may be moved while the cellular panel 20 is stationary. In an example shown in FIG. 6, the cellular panel 20 may be moved to achieve the tilt angle φ, while the radiation source 44 and the detector 46 are stationary. In another example, all of the cellular panel 20, the radiation source 44, and the detector 46 may be moved to achieve the tilt angle φ.

Figure 7:
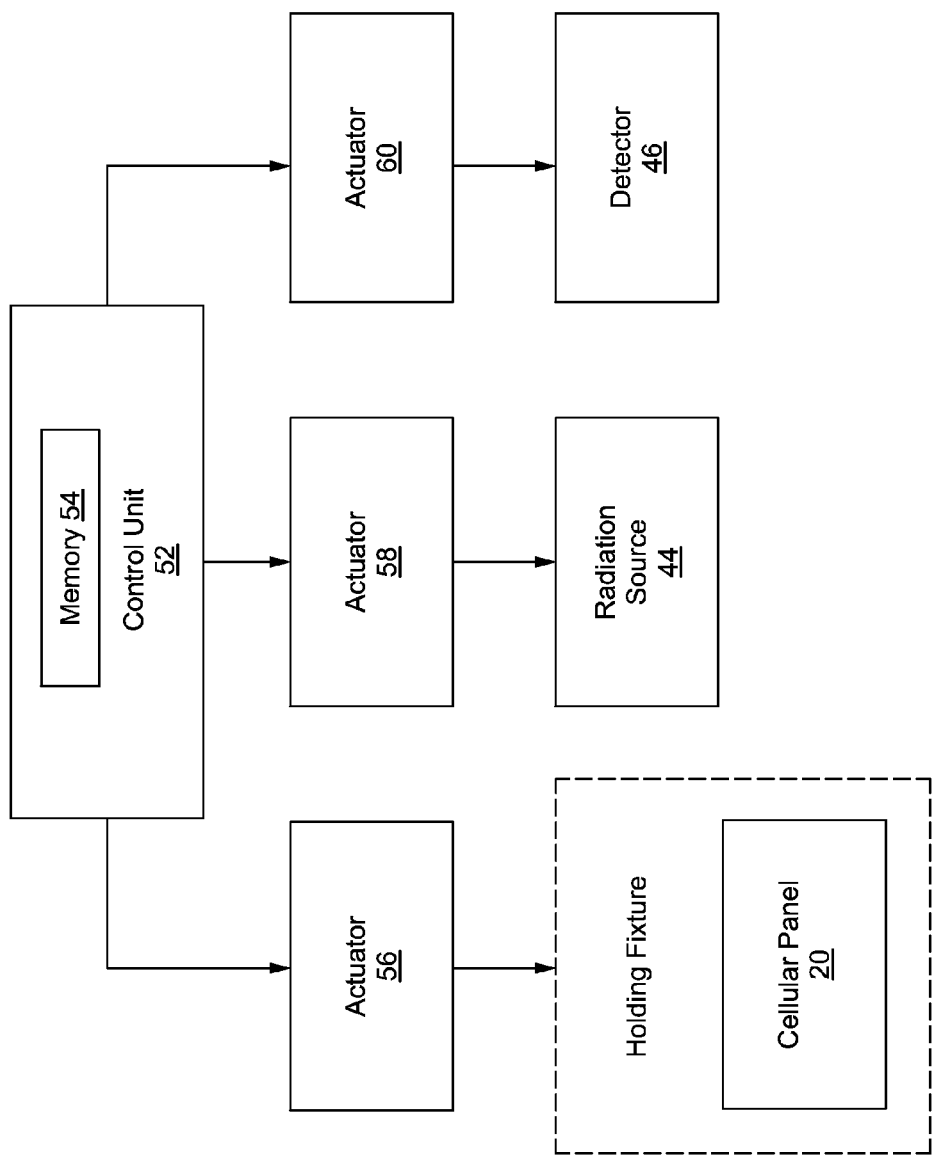
FIG. 7 is a schematic view of an imaging system, in accordance with another embodiment.

Referring now to FIG. 7, with continued reference to FIGS. 1-6, the imaging system 40 includes a control unit 52 in operative communication with the radiation source 44 and the detector 46. The control unit 52 is implemented using one or more of a processor, such as a "computer processor," or a processor-based device that is included or associated with a non-transitory computer readable storage medium having stored thereon computer-executable instructions. One or more algorithms may be programmed into a memory 54 associated with the control unit 52. The memory 54 is provided within and/or external to the control unit 52, and may comprise a non-volatile memory. It is to be understood that the control unit 52 may include other hardware, software, firmware, and combinations thereof.

Furthermore, a value for the tilt angle φ can be programmed and stored in the memory 54 associated with the control unit 52. The control unit 52 is configured to rotate the radiation source 44, the detector 46, and/or the cellular panel 20 to implement the tilt angle φ. For example, the control unit 52 may be in communication with actuators 56, 58, 60 associated with the cellular panel 20, the radiation source 44 and the detector 46, respectively. The control unit 52 is programmed to send signals to one or more of the actuators 56, 58, 60 to rotate the radiation source 44, the detector 46, and/or the cellular panel 20 according to the preprogrammed value for the tilt angle φ. In addition, each of the actuators 56, 58, 60 may include a sensor configured to detect a position of the cellular panel 20, the radiation source 44 and the detector 46 in order to verify an actual tilt angle.

Figure 8:
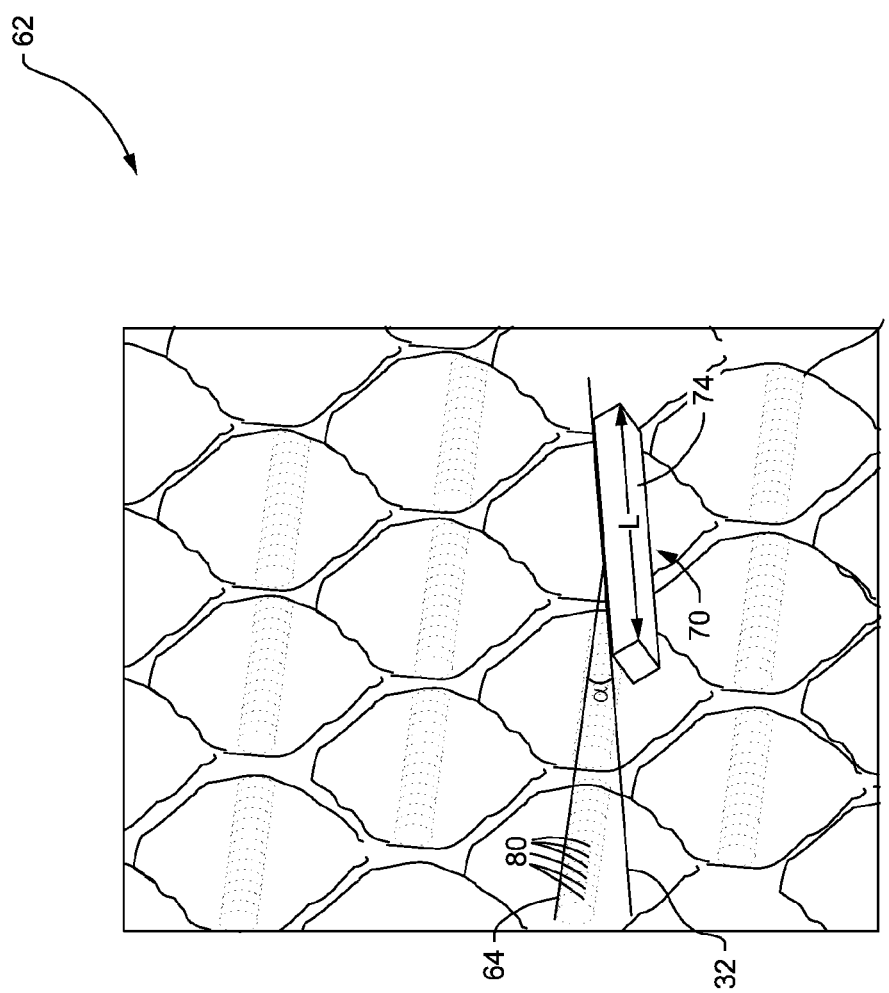
FIG. 8 is an example X-ray image of an interior of a cellular panel obtained when the cellular panel is positioned at a tilt angle relative to a radiation source and a detector, in accordance with another embodiment.

When the cellular panel 20 is positioned at the tilt angle φ relative to the line 50 extending between the radiation source 44 and the detector 46, radiation from the radiation source 44 is transmitted through the cellular panel 20 to the detector 46 to obtain an image, such as, the example image 62 shown in FIG. 8. From the obtained image 62, a projected shear angle α is determined. The projected shear angle α refers to a projection of the true or actual shear angle θ onto the two dimensional plane of the image 62 obtained when the cellular panel 20 is at the tilt angle φ. For instance, the projected shear angle α may be identified in the image 62 between the line 32 perpendicular to the facesheets 22, 24 and a line 64 parallel to, coincident, or aligned with the interior walls 30.

A reference element 70 may assist in identifying the line 32 perpendicular to the facesheets 22, 24, as shown in FIGS. 1, 3, 5, 6, and 8. The reference element 70 may comprise, for example, a nail including a head 72 with a shaft 74 perpendicularly extending therefrom. However, other objects may be used to assist in identification of the line 32 perpendicular to the facesheets 22, 24. The head 72 of the reference element 70 is temporarily attached to an outer surface 76 of one of the facesheets 22, 24.

With the head 72 of the reference element 70 oriented parallel or tangent to the outer surface 76 of the facesheet 22, a length L of the shaft 74 is perpendicular to the facesheet 22. After the image 62, in FIG. 8, is obtained with the reference element 70 attached to the facesheet 22, the shaft 74 of the reference element 70 may be used as a basis of identification for the line 32 perpendicular to the facesheets 22, 24 in the image 62. More specifically, the line 32 may follow and extend from the length L of the shaft 74 throughout the image 62. However, other techniques may be used to identify in the image 62 the line 32 perpendicular to the facesheets 22, 24.

Figure 9:
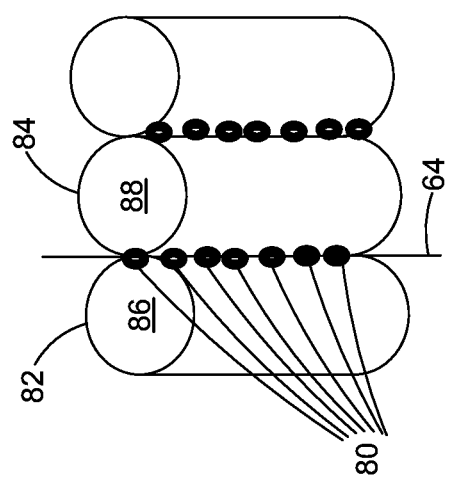
FIG. 9 is a schematic view of cells of the core of FIG. 2 attached by a plurality of node welds.

Referring now to FIG. 9, with continued reference to FIGS. 1-8, a series of node welds 80 between interior walls 82, 84 of two adjacent cells 86, 88, respectively, may be used as a basis of identification for the line 64 parallel to the interior walls 30. The series of node welds 80 comprise points along a height of the walls 82, 84 where the two cells 86, 88 are bonded together. In the image 62 of FIG. 8, by identifying the series of node welds 80, a straight line through each of the node welds 80 may comprise the line 64 parallel to the interior walls 30. However, other techniques may be used to identify in the image 62 the line 64 parallel to the interior walls 30.

In addition, the control unit 52 may be configured to identify in the image 62 the line 32 perpendicular to the facesheets 22, 24 and the line 64 parallel to the interior walls 30, such as, by using boundary detection. A user of the imaging system 40 may also identify the lines 32, 64 in the image 62, such as, on a screen or other user interface depicting the image 62. Moreover, the control unit 52 may be further configured to measure the projected shear angle α between the lines 32, 64 identified in the obtained image 62. However, the projected shear angle α may also be measured manually by the user.

Figure 10:
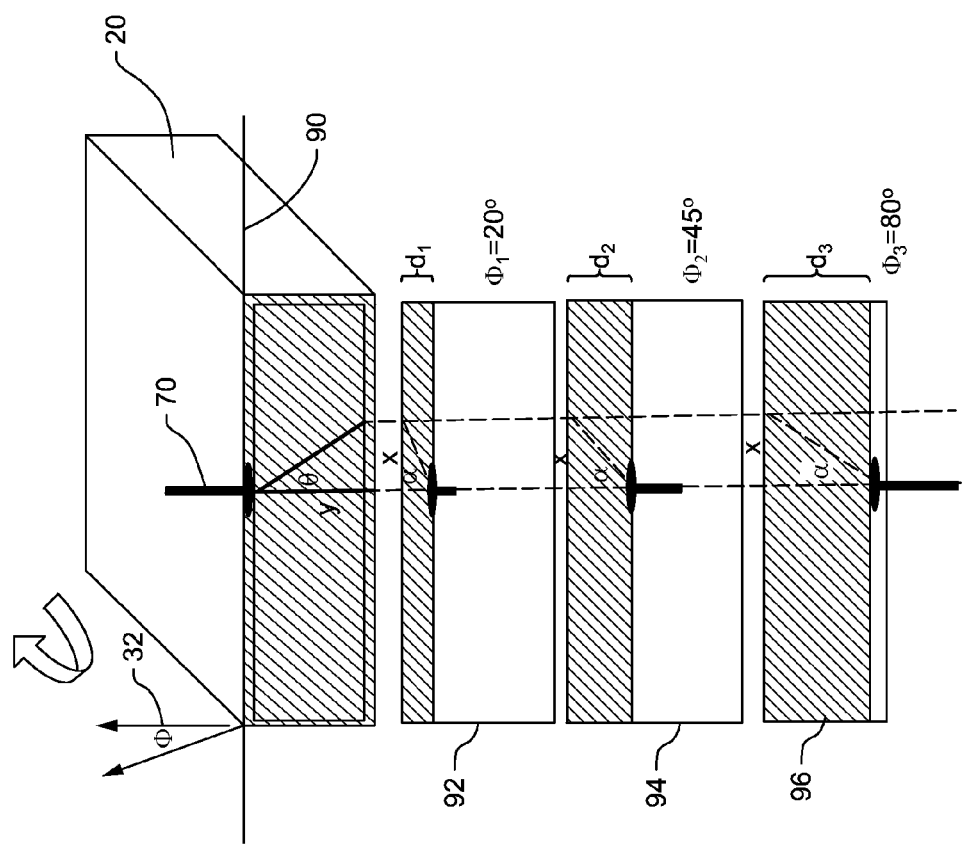
FIG. 10 is a diagrammatic view of exemplary images of a cellular panel obtained when the cellular panel is positioned at various tilt angles, in accordance with another embodiment.

Turning now to FIG. 10, with continued reference to FIGS. 1-9, the actual shear angle θ is determined using the tilt angle φ and the projected shear angle α. More specifically, the tilt angle φ is achieved either by rotation of the cellular panel 20 about an axis 90, rotation of the radiation source 44 and the detector 46 about the axis 90, or a combination thereof. After an image, such as an X-ray image, is obtained at a tilt angle φ, the projected shear angle α represented in the obtained image may be determined based on the following equation:

$$\tan \alpha = x/d \quad [2]$$

where α is the projected shear angle; x is the projected width of the interior wall 30 onto one of the facesheets 22, 24 when the line 50 extending between the radiation source 44 and the detector 46 is parallel to, coincident, or aligned with the line 32 perpendicular to the facesheets 22, 24; and d is a projected thickness of the cellular panel 20 onto the two dimensional plane of the image obtained at the tilt angle φ. As shown in images 92, 94, 96 obtained at various tilt angles $φ_1, φ_2, φ_3$, respectively, the projected width x of the interior wall 30 stays the same in each image, while the projected thicknesses $d_1, d_2, d_3$, respectively, of the cellular panel 20 changes in each image as the tilt angle φ changes.

Figure 11:
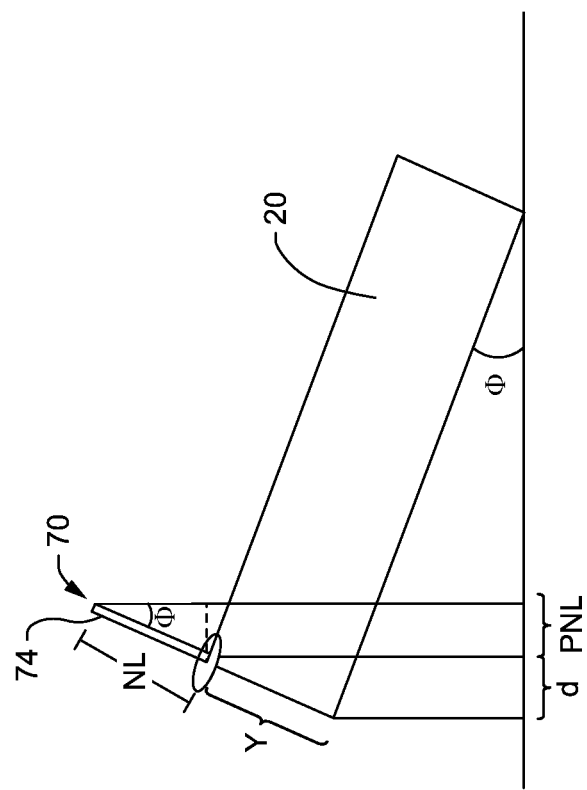
FIG. 11 is a diagrammatic view of a cellular panel and a reference element positioned at a tilt angle, in accordance with another embodiment.

Referring now to FIG. 11, with continued reference to FIGS. 1-10, the following equation for the tilt angle φ is derived:

$$\sin φ = d/y \quad [3]$$

where φ is the tilt angle, d is the projected thickness of the cellular panel 20, and y is the thickness of the cellular panel 20. In addition, using the reference element 70, another equation for the tilt angle φ is derived from FIG. 11 as follows:

$$\sin φ = PNL/NL \quad [4]$$

where φ is the tilt angle, PNL is a projected nail length or a projected length of the shaft 74 of the reference element 70, and NL is an actual nail length or an actual length of the shaft 74 of the reference element 70. A user can use the equations [3] and [4] above to calculate the actual tilt angle.

Moreover, based on the equations [3] and [4] above for the tilt angle φ, the following equation for the projected thickness of the cellular panel 20 is derived:

$$d = PNL/NL * y \quad [5]$$

where d is the projected thickness of the cellular panel 20, PNL is the projected length of the shaft 74 of the reference element 70, NL is the actual length of the shaft 74 of the reference element 70, and y is the thickness of the cellular panel 20.

By substituting the equation [5] for the projected thickness d of the cellular panel 20 into the equation [2] above for the projected shear angle α, the following equation for the thickness y of the cellular panel 20 is derived:

$$y = (NL * x)/(PNL * \tan \alpha) \quad [6]$$

where y is the thickness of the cellular panel 20; NL is the actual length of the shaft 74 of the reference element 70; x is the projected width of the interior wall 30 onto one of the facesheets 22, 24 when the line 50 extending between the radiation source 44 and the detector 46 is parallel to, coincident, or aligned with the line 32 perpendicular to the facesheets 22, 24; PNL is the projected length of the shaft 74 of the reference element 70; and a is the projected shear angle. Furthermore, substituting the equation [4] above for the tilt angle φ and the equation [6] above for the thickness y of the cellular panel 20 into the equation [1] above for the actual shear angle θ results in the following equation:

$$\tan θ = \tan \alpha * \sin φ \quad [7]$$

where θ is the actual shear angle, α is the projected shear angle, and φ is the tilt angle. Thus, with known values for the projected shear angle α and the tilt angle φ, the user can manually determine the actual shear angle θ using the equation [7] above.

In another embodiment, the equation [7] above is programmed into the memory 54 associated with the control unit 52. For instance, using the detected tilt angle φ from the sensor and the projected shear angle α previously measured using boundary detection, the control unit 52 can be configured to use the equation [7] above to determine the actual shear angle θ. However, other equations than those above may also be used to determine the actual shear angle θ based on the projected shear angle α. In so doing, the actual shear angle θ is quantified using a non-destructive inspection technique for the cellular panel 20.

Furthermore, the user can determine whether the cellular panel 20 is within predetermined specifications based on the determined actual shear angle θ. More specifically, the user can compare the determined actual shear angle θ to a range of predetermined specification tolerances for the shear angle of the cellular panel 20. In another example, the control unit 52 can be configured to determine whether the cellular panel 20 meets predetermined specification tolerances for the shear angle. For instance, predetermined specification tolerances for the shear angle of the cellular panel 20 can be programmed into the memory 54 associated with the control unit 52. The control unit 52 can further be configured to compare the determined actual shear angle θ to the preprogrammed data, verify whether the determined actual shear angle θ is within the predetermined specification tolerances, and notify the user.

Figure 12:
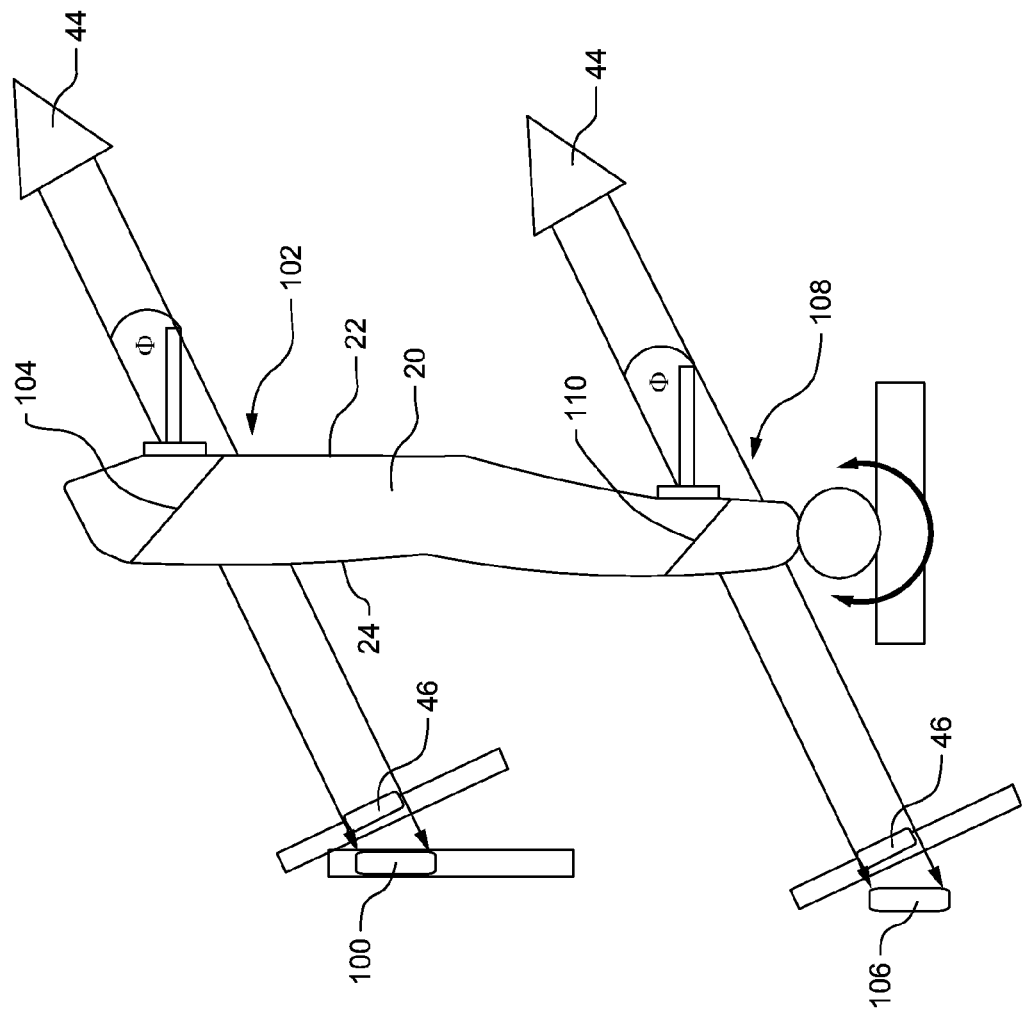
FIG. 12 is a diagrammatic view of an imaging system obtaining images of a cellular panel at two different locations on the cellular panel, in accordance with another embodiment.

Referring now to FIG. 12, with continued reference to FIGS. 1-11, more than one image is obtained at different locations on the cellular panel 20. By obtaining various images of different interior walls, shear effects throughout the entire cellular panel 20 can be measured and quantified. For instance, a first image 100 of a first interior wall 104 is obtained at a first location 102, and a second image 106 of a second interior wall 110 is obtained at a second location 108. A first shear angle is determined from the first image 100, and a second shear angle is determined from the second image 106. To obtain an average shear angle for the cellular panel 20, the first shear angle and the second shear angle is averaged together. Furthermore, more than two images of more than two interior walls at more than two different locations may be obtained in order to get multiple shear angles for the cellular panel 20. In so doing, the average shear angle can be obtained by averaging the multiple shear angles together.

Figure 13:
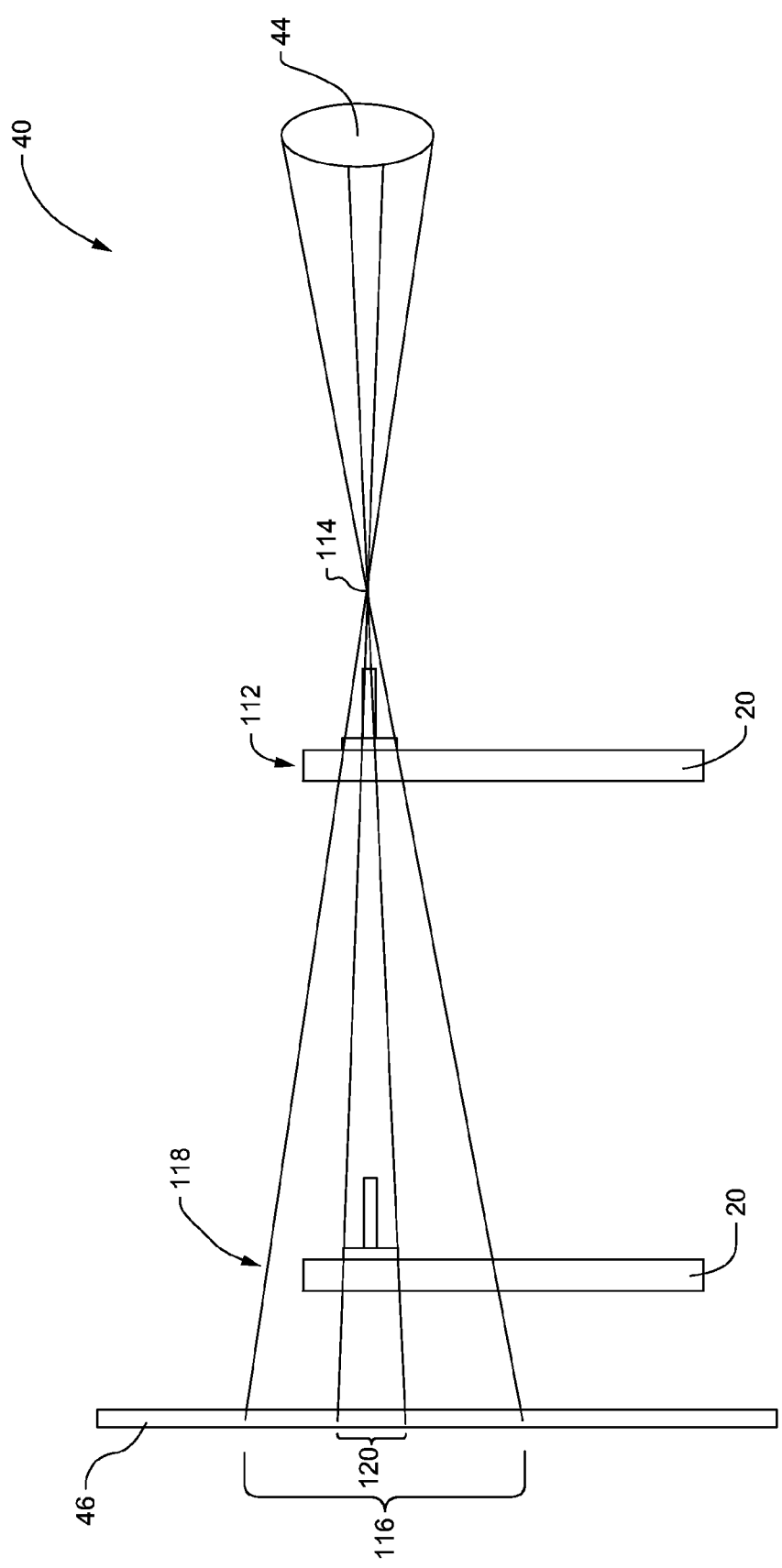
FIG. 13 is a diagrammatic view of magnification effects of an imaging system, in accordance with another embodiment.

Furthermore, as shown in FIG. 13, the cellular panel 20 is positioned closer to the detector 46 than the radiation source 44, in accordance with another embodiment. For example, when the cellular panel 20 is not positioned closer to the detector 46 than the radiation source 44, such as, at a first position 112 near a focal point 114 of the imaging system 40, a first projected image 116 on the detector 46 may be magnified. When the cellular panel 20 is positioned closer to the detector 46 than the radiation source 44, such as, at a second position 118, magnification errors of a second projected image 120 may be reduced. However, other configurations and arrangements of the cellular panel relative to the radiation source 44 and the detector 46 may be used.

It is to be understood that the imaging system 40 and techniques disclosed herein for shear angle quantification may be used on any object or part, and are not limited to cellular panels.

INDUSTRIAL APPLICABILITY

In general, the foregoing disclosure finds utility in various applications relating to cellular panels. The disclosed system and techniques provide non-destructive inspection of cellular panels and shear angle quantification of interior walls within a cellular panel. More specifically, the disclosed system and techniques use radiography to measure a shear angle of one or more interior walls within the cellular panel. In particular, by obtaining an image of the interior wall while the cellular panel is positioned at a tilt angle relative to the radiation source and detector, a user or control unit determines the actual shear angle through projected to true shear angle conversion. In so doing, the user or control unit can determine whether the cellular panel is within specification tolerances.

Figure 14:
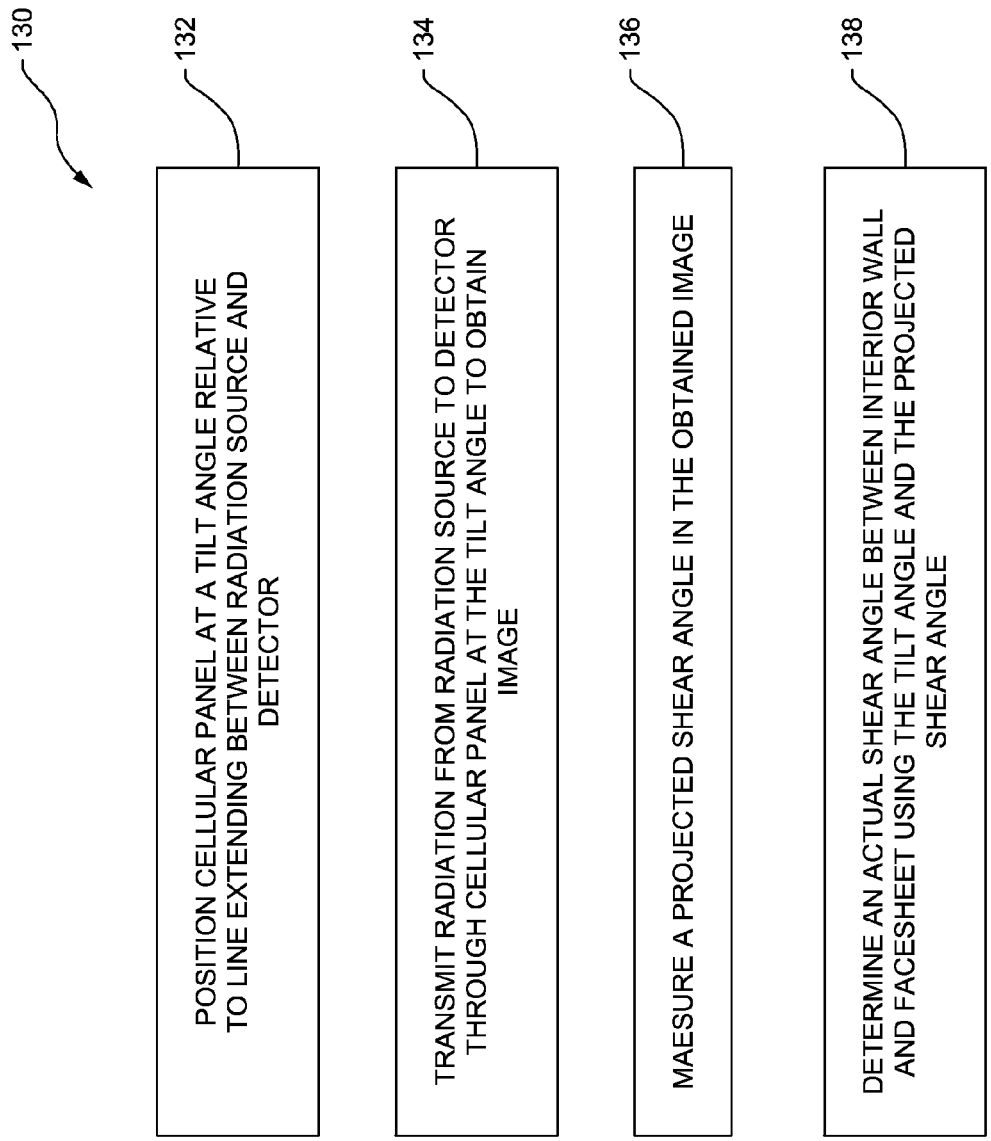
FIG. 14 is a flowchart illustrating a process for determining an actual shear angle between an interior wall and a facesheet of a cellular panel using an imaging system, in accordance with another embodiment.

Turning now to FIG. 14, with continued reference to FIGS. 1-13, a process 130 for determining an actual shear angle θ between an interior wall 30 and a facesheet 22, 24 of a cellular panel 20 using an imaging system 40 is shown, in accordance with another embodiment of the present disclosure. At block 132, the cellular panel 20 is positioned at a tilt angle φ relative to a line 50 extending between the radiation source 44 and the detector 46. Radiation is transmitted from the radiation source 44 to the detector 46 through the cellular panel 20 at the tilt angle φ to obtain an image, at block 134. A projected shear angle α is measured in the obtained image, at block 136. At block 138, the actual shear angle θ between the interior wall θ and the facesheet 22, 24 is determined using the tilt angle φ and the projected shear angle α.

It is to be understood that the flowchart in FIG. 14 is shown and described as an example only to assist in disclosing the features of the disclosed system and techniques, and that more or less steps than that shown may be included in the process corresponding to the various features described above for the disclosed system without departing from the scope of the disclosure.

While the foregoing detailed description has been given and provided with respect to certain specific embodiments, it is to be understood that the scope of the disclosure should not be limited to such embodiments, but that the same are provided simply for enablement and best mode purposes. The breadth and spirit of the present disclosure is broader than the embodiments specifically disclosed and encompassed within the claims appended hereto. Moreover, while some features are described in conjunction with certain specific embodiments, these features are not limited to use with only the embodiment with which they are described, but instead may be used together with or separate from, other features disclosed in conjunction with alternate embodiments.

What is claimed is:

1. A method for determining an actual shear angle between an interior wall and a facesheet of a cellular panel using an imaging system, the imaging system including a radiation source and a detector diametrically opposed to the radiation source, the method comprising:
   positioning the cellular panel at a tilt angle relative to a line extending between the radiation source and the detector;
   transmitting radiation from the radiation source to the detector through the cellular panel at the tilt angle to obtain an image;
   measuring a projected shear angle in the obtained image;
   determining the actual shear angle between the interior wall and the facesheet using the tilt angle and the projected shear angle; and
   determining if the cellular panel is within predetermined specifications based on the determined actual shear angle.

2. The method of claim 1, further comprising rotating the radiation source and the detector while the cellular panel is stationary to achieve the tilt angle.

3. The method of claim 1, further comprising rotating the cellular panel while the radiation source and the detector are stationary to achieve the tilt angle.

4. The method of claim 1, wherein the tilt angle is between an inclusive range of twenty degrees to fifty degrees (20°-50°).

5. The method of claim 1, further comprising using X-ray radiation as the radiation.

6. The method of claim 1, further comprising calculating the actual shear angle using the tilt angle and the projected shear angle.

7. The method of claim 1, further comprising obtaining a first image of a first interior wall at a first location to determine a first actual shear angle, and obtaining a second image of a second interior wall at a second location to determine a second actual shear angle.

8. The method of claim 7, further comprising averaging the first actual shear angle and the second actual shear angle to obtain an average shear angle for the cellular panel.

9. The method of claim 1, further comprising identifying the projected shear angle between a line perpendicular to the facesheet and a line extending through node welds of the interior wall.

10. The method of claim 9, further comprising a user of the imaging system determining the projected shear angle.

11. The method of claim 9, further comprising the imaging system automatically determining the projected shear angle using boundary detection.

12. The method of claim 9, further comprising placing a reference element on a surface of the facesheet to assist in identification of the line perpendicular to the facesheet.

13. An imaging system for determining an actual shear angle between an interior wall and a facesheet of a cellular panel, the imaging system comprising:
   a radiation source;
   a detector diametrically opposed to the radiation source and configured to detect radiation transmitted through the cellular panel from the radiation source; and
   at least one computer processor in operative communication with the radiation source and the detector, the at least one computer processor configured to:
      position the radiation source and the detector at a tilt angle relative to a line perpendicular to the facesheet of the cellular panel,
      transmit radiation from the radiation source through the cellular panel to the detector to obtain an image of the interior wall of the cellular panel,
      identify in the obtained image the line perpendicular to the facesheet,
      identify in the obtained image a line parallel to the interior wall,
      measure in the obtained image a projected shear angle between the line perpendicular to the facesheet and the line parallel to the interior wall,
      determine an actual shear angle between the facesheet and the interior wall using the tilt angle and the projected shear angle, and
      determine if the cellular panel is within predetermined specifications based on the determined actual shear angle.

14. The imaging system of claim 13, wherein the cellular panel is positioned closer to the detector than the radiation source.

15. The imaging system of claim 13, wherein the at least one computer processor is configured to use node welds of the interior wall in the obtained image to identify the line parallel to the interior wall.

16. The imaging system of claim 13, wherein the at least one computer processor is configured to use a reference element attached to a surface of the facesheet in the obtained image to identify the line perpendicular to the facesheet.

17. An automated method for determining an actual shear angle between an interior wall and a facesheet of a cellular panel using an imaging system including a radiation source, a detector diametrically opposed to the radiation source, and at least one computer processor in operative communication with the radiation source and the detector, the automated method comprising:

moving the radiation source and the detector such that a line extending between the radiation source and the detector is at a tilt angle relative to a line perpendicular to the facesheet;

acquiring an image of the interior wall by transmitting radiation from the radiation source through the cellular panel to the detector;

identifying in the acquired image a projected shear angle between the line perpendicular to the facesheet and a line extending through node welds of the interior wall;

measuring the projected shear angle;

determining an actual shear angle between the facesheet and the interior wall based on the tilt angle and the measured projected shear angle, and determining if the cellular panel is within predetermined specifications based on the determined actual shear angle.

18. The automated method of claim 17, further comprising using the following equation to determine the actual shear angle:

$$\tan \theta = \tan \alpha * \sin \varphi$$

where $\theta$ is the actual shear angle, $\alpha$ is the measured projected shear angle, and $\varphi$ is the tilt angle.

19. The automated method of claim 17, further comprising storing a value for the tilt angle between an inclusive range of twenty degrees to fifty degrees (20°-50°) in a memory associated with the at least one computer processor.

* * * * *